(12) United States Patent
Corcoran et al.

(10) Patent No.: US 7,905,901 B2
(45) Date of Patent: Mar. 15, 2011

(54) SELF-CENTERING OCCLUSION DEVICE

(75) Inventors: Michael P. Corcoran, Woodbury, MN (US); Joseph A. Marino, Apple Valley, MN (US)

(73) Assignee: Cardia, Inc., Burnsville, MN (US)

( * ) Notice: Subject to any disclaimer, the term of this patent is extended or adjusted under 35 U.S.C. 154(b) by 408 days.

(21) Appl. No.: 10/998,422

(22) Filed: Nov. 29, 2004

(65) Prior Publication Data

US 2006/0116710 A1 Jun. 1, 2006

(51) Int. Cl.
*A61B 17/03* (2006.01)
(52) U.S. Cl. .......................................... 606/213
(58) Field of Classification Search .................. 606/215, 606/216, 232, 151–153, 213, 157, 200; 623/23.72; 128/830, 833, 831, 843
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,917,089 A | 4/1990 | Sideris | |
| 5,108,420 A * | 4/1992 | Marks | 606/213 |
| 5,171,259 A | 12/1992 | Inoue | |
| 5,284,488 A | 2/1994 | Sideris | |
| 5,334,137 A | 8/1994 | Freeman | |
| 5,334,217 A | 8/1994 | Das | |
| 5,382,260 A | 1/1995 | Dormandy, Jr. et al. | |
| 5,397,331 A | 3/1995 | Himpens et al. | |
| 5,425,744 A | 6/1995 | Fagain et al. | |
| 5,433,727 A | 7/1995 | Sideris | |
| 5,451,235 A | 9/1995 | Lock et al. | |
| 5,634,936 A | 6/1997 | Linden et al. | |
| 5,649,950 A | 7/1997 | Bourne et al. | |
| 5,702,421 A | 12/1997 | Schneidt | |
| 5,709,707 A | 1/1998 | Lock et al. | |
| 5,725,552 A | 3/1998 | Kotula et al. | |
| 5,741,297 A | 4/1998 | Simon | |
| 5,853,422 A * | 12/1998 | Huebsch et al. | 606/213 |
| 5,904,703 A | 5/1999 | Gilson | |
| 6,024,756 A | 2/2000 | Huebsch et al. | |
| 6,174,322 B1 * | 1/2001 | Schneidt | 606/213 |
| 6,206,907 B1 | 3/2001 | Marino et al. | |
| 6,355,052 B1 * | 3/2002 | Neuss et al. | 606/213 |
| 6,379,368 B1 | 4/2002 | Corcoran et al. | |
| 2003/0171774 A1 * | 9/2003 | Freudenthal et al. | 606/213 |
| 2004/0093022 A9 * | 5/2004 | Kurz et al. | 606/213 |

FOREIGN PATENT DOCUMENTS

| | | |
|---|---|---|
| DE | 233 303 A1 | 2/1986 |
| DE | 4222291 | 1/1994 |
| EP | 0 362 113 A1 | 4/1990 |
| EP | 0 541 063 A2 | 12/1993 |
| EP | 0 541 063 A3 | 12/1993 |
| EP | 0 541 063 B1 | 2/1998 |
| GB | 2 269 321 A | 9/1994 |

\* cited by examiner

*Primary Examiner* — Elizabeth Houston
(74) *Attorney, Agent, or Firm* — Kinney & Lange, P.A.

(57) ABSTRACT

This invention relates to an occlusion device for the closure of physical defects. The occlusion device is capable of self-centering itself in the defect. This allows the center of the occluder to remain properly positioned in the defect, while maintaining a low profile against the tissue.

20 Claims, 6 Drawing Sheets

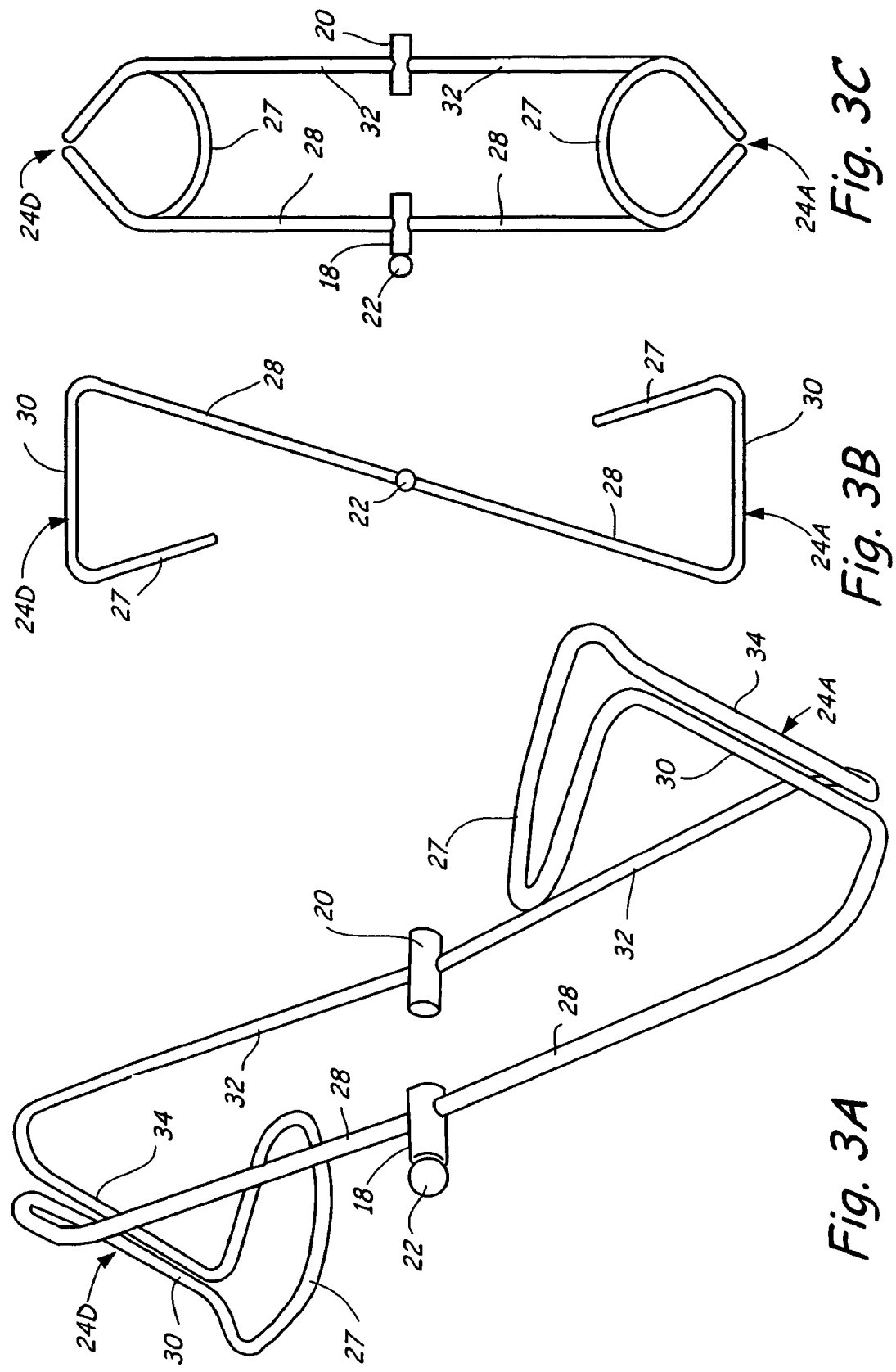

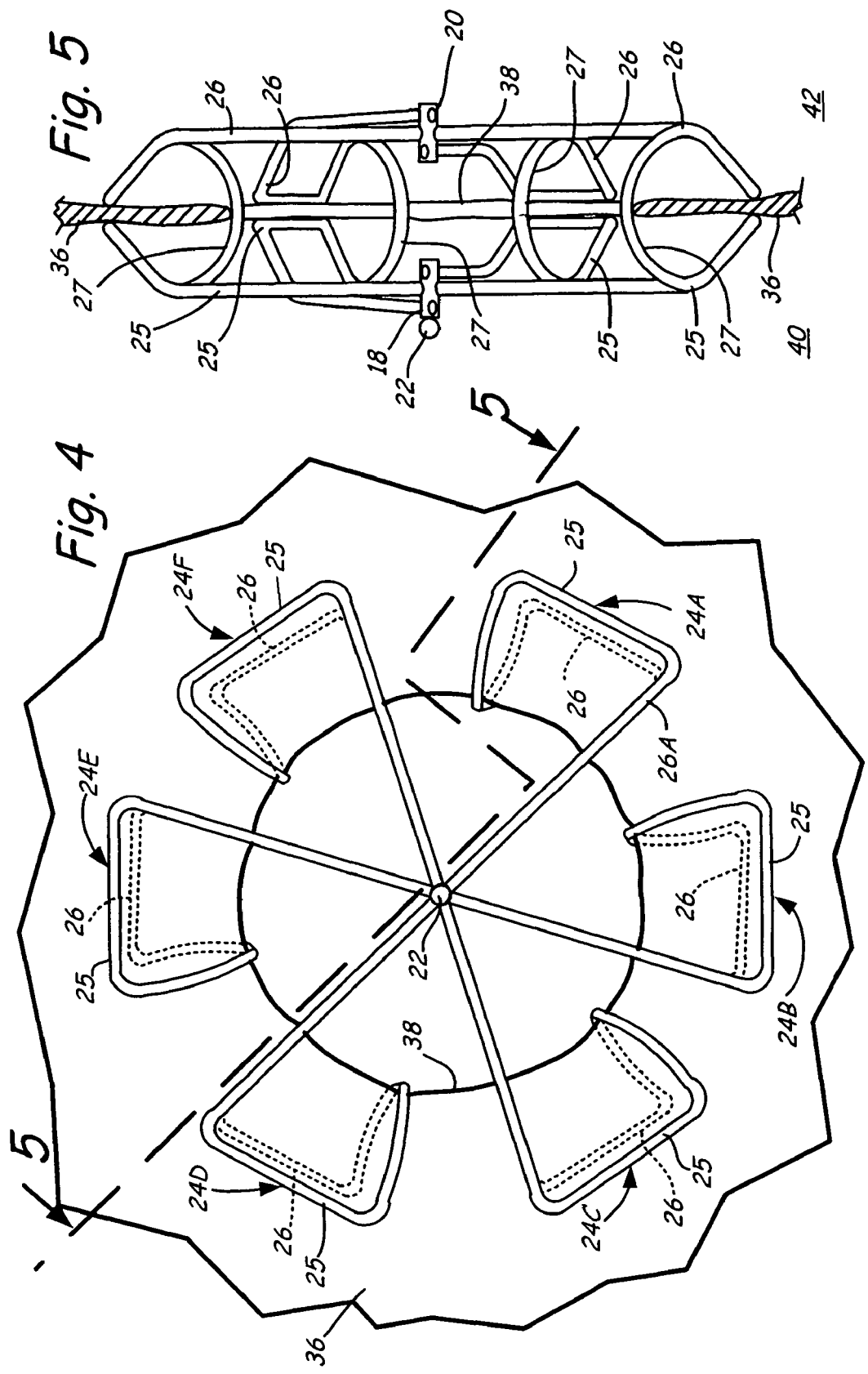

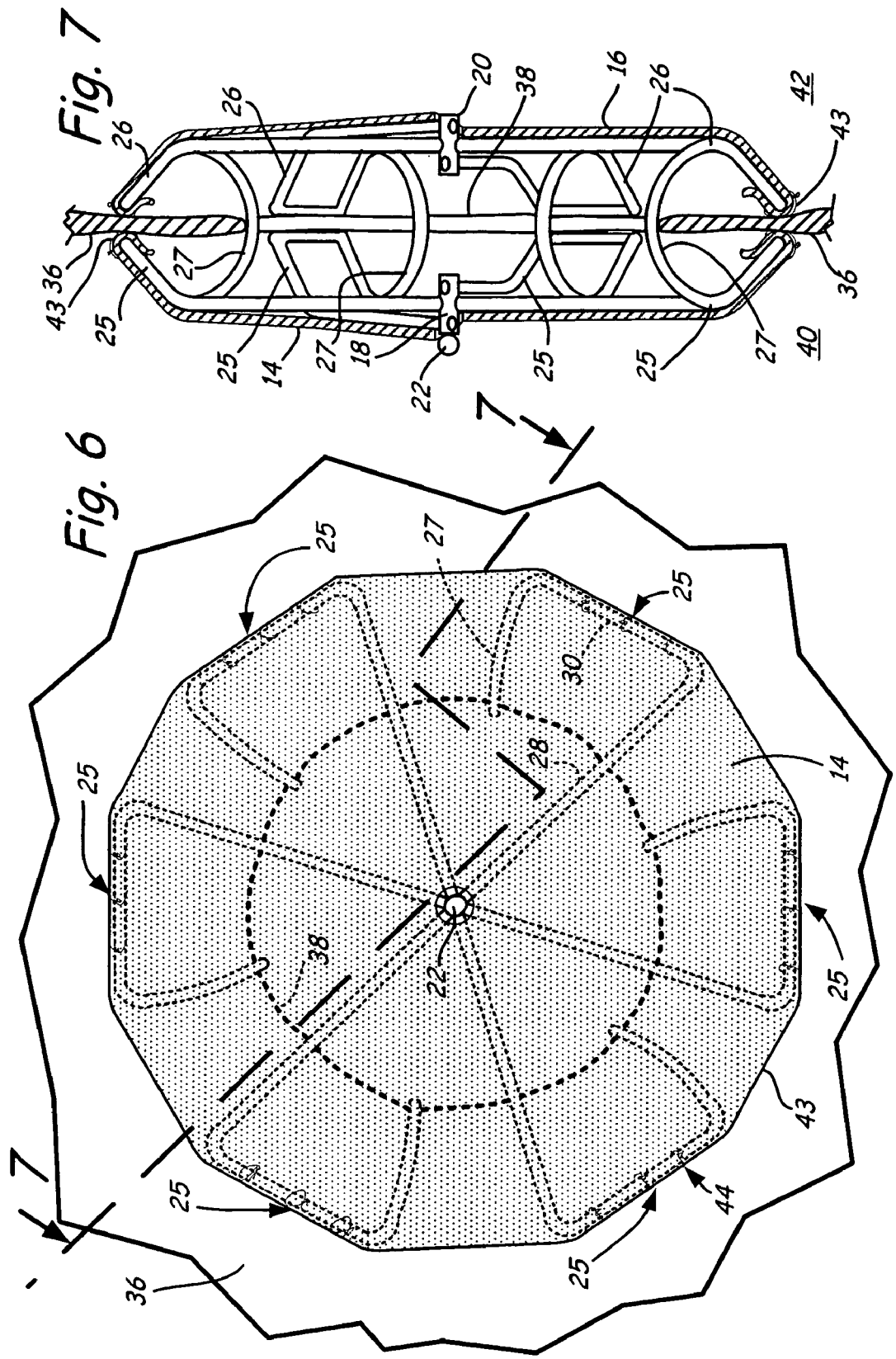

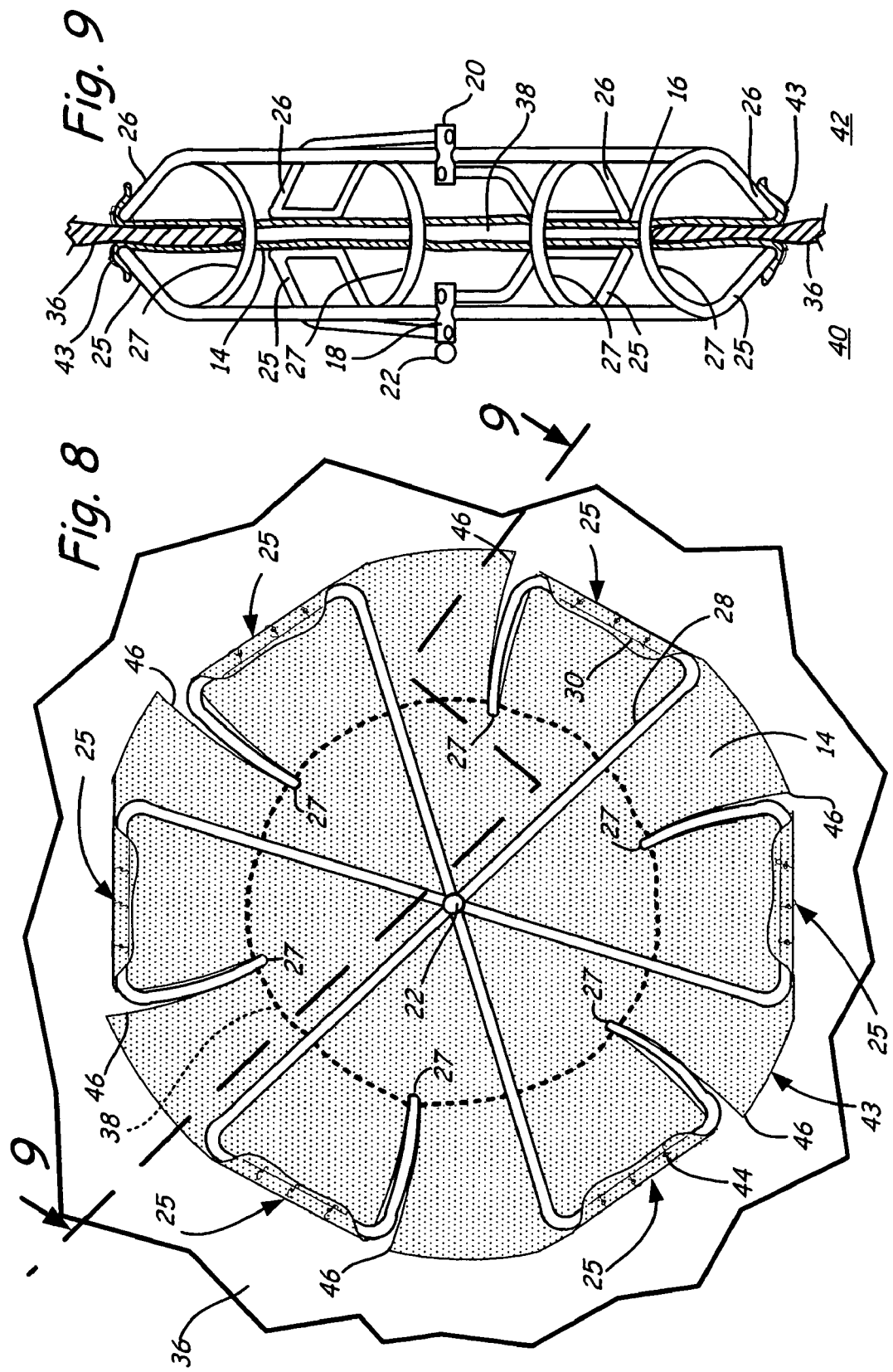

SELF-CENTERING OCCLUSION DEVICE

CROSS-REFERENCE TO RELATED APPLICATION(S)

None.

BACKGROUND OF THE INVENTION

This invention relates to an occlusion device for the closure of physical apertures, such as vascular or septal apertures. More specifically, this invention relates to an occlusion device for closing an aperture that is capable of self-centering in the aperture.

The heart is generally comprised of four chambers: the left and right atrium, and the left and right ventricle. Separating the left and right sides of the heart are two walls, or septa. The wall between the two atria is the interatrial septum and the wall between the two ventricles is the interventricular septum. There are several defects which can affect the septa of both children and adults, including patent ductus arteriosus, patent foramen ovale, atrial septal defects (ASDs), and ventricular septal defects (VSDs). Although the causes and physical aspects of these defects vary by type, each of these defects is generally an aperture, flap, or hole in the septum that allows blood to shunt between chambers in the heart where there is no blood flow in a normal, healthy heart. This abnormal shunt can cause a variety of health problems.

Normally, permanently repairing certain cardiac defects in adults and children requires open heart surgery, which is a risky, painful, and expensive procedure. Surgically closing an aperture in the heart requires the patient to undergo general anesthesia and requires opening of the chest cavity. The patient may spend several days in the hospital and thereafter may take several weeks to recover before being able to return to normal levels of activity.

To avoid the risks and discomfort associated with open heart surgery, modern occlusion devices have been developed that are small, implantable devices capable of being delivered to the heart through a catheter. These devices are used to close the aperture, but do not require surgery. Rather than surgery, a catheter inserted into a major blood vessel, and an occlusion device is moved through the catheter to the treatment site, where it can then be deployed at the defect. This procedure can be performed in a cardiac cathlab, and reduces the risks, pain, and long recovery time associated with open heart surgery.

There are currently several types of occlusion devices capable of being inserted via a catheter including button devices, collapsible umbrella-like structures, and plug-like devices. These modern occlusion devices can repair a wide range of cardiac defects, including patent foramen ovale, patent ductus arteriosus, atrial septal defects, ventricular septal defects, and may occlude other cardiac and non-cardiac apertures.

One form of occlusion device generally has a first side, a second side, and a center section. Once the occluder is deployed, the first side is positioned on one side of the aperture to be occluded, and the second side is positioned on the other side of the aperture. The occluder's center section extends through the center of the defect or aperture being occluded. The first and second sides of the occlusion device serve to occlude the aperture on the respective sides of the aperture. Because the center section of the occlusion device may be small relative to the size of the aperture to be occluded, it is a challenge to ensure the occlusion device is properly centered across the aperture.

As mentioned, several types of septal defects exist. In addition, the size and shape of each defect and the size and shape of the heart varies from patient to patient. It is important that any occlusion device be properly centered in the defect so that the device is most effective at sealing the aperture. This is particularly true for larger defects. As such, it is important for the occlusion device to be centered in the defect to ensure the left and right sides of the device properly cover the aperture. If the defect is not properly occluded, blood will continue to shunt through the defect, which lessens the effectiveness of the device.

It is also important to reduce the overall bulk of the occlusion device as much as possible, while still retaining its ability to properly occlude the aperture or defect. This is essential for the treatment of children because they have smaller vessels than adults. The occlusion device must collapse down to a very small diameter, so it will fit in a catheter narrow enough to thread though a child's tiny vessels. It is also desirable that the occlusion device maintain a low profile after placed at the site of the defect, in order to minimize corrosion of the metal and potential blood clots.

Thus, there is a need in the art for an occlusion device which has a centering system to improve the ability of the device to be centered in the defect, while also having the ability to collapse to a small diameter and maintain a low profile against the septum.

BRIEF SUMMARY OF THE INVENTION

The present invention provides a self-centering occlusion device that keeps the occluder properly centered in an aperture. This allows the center of the occluder to remain properly positioned within the aperture so that the first and second sides cover the entire aperture, while maintaining a low profile against the septum. This reduces the chance of blood shunting through the aperture and therefore increases the effectiveness of the occluding device. The present invention also has the ability to collapse down to a small diameter, so it can be used in treating septal defects in children. The self-centering occlusion device is comprised of a frame for centering the device in a defect. The frame is shaped to have first contact locations for contacting tissue on a first side of the defect, second contact locations for contacting tissue on a second side of the defect, and centering arcs extending from the first contact locations to the second contact locations.

BRIEF DESCRIPTION OF THE DRAWINGS

FIG. 3A is a perspective view of opposing arm pairs of the occlusion device.

FIG. 3B is a proximal end view of the opposing arm pairs of the occlusion device.

FIG. 3C is a side view of the opposing arm pairs of the occlusion device.

FIG. 4 is a proximal end view of a wire frame of an occlusion device without the occluding sheets attached illustrating the device deployed across a defect.

FIG. 5 is a sectional view of the wire frame of the occlusion device without the occluding sheets attached along section 5-5 of FIG. 4 as it is deployed across a defect.

FIG. 6 is a proximal end view of an occlusion device showing a placement of an occluding sheet on the outside of the wire frame as the device is deployed across a defect.

FIG. 7 is a sectional view of the occlusion device along section 7-7 of FIG. 6 showing the placement of the occluding sheet on the outside of the wire frame as the device is deployed across the defect.

FIG. 8 is a proximal end view of an occlusion device showing a placement of an occluding sheet on the inside of the wire frame as the device is deployed across a defect.

FIG. 9 is a sectional view of the occlusion device along section 9-9 of FIG. 8 showing the placement of the occluding sheet on the inside of the wire frame as the device is deployed across the defect.

DETAILED DESCRIPTION

Figure 1:
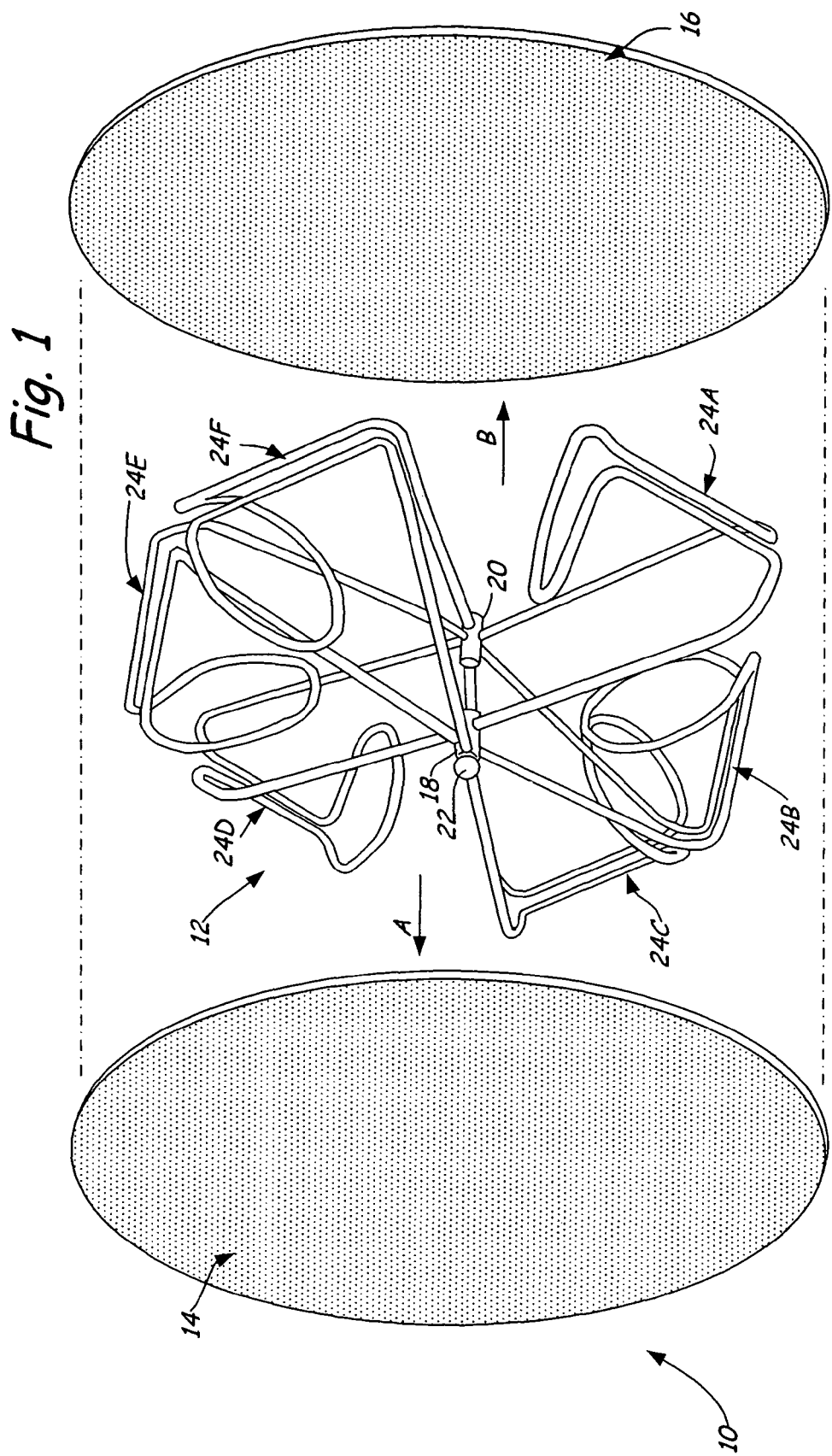
FIG. 1 is an exploded perspective view of an occlusion device of the present invention.

FIG. 1 is an exploded view of occlusion device 10. Occlusion device 10 comprises wire frame 12, proximal sheet 14, and distal sheet 16. Wire frame 12 comprises proximal center post 18, distal center post 20, grasping knob 22, and six arm pairs 24A-24F.

Grasping knob 22 on proximal center post 18 is configured to allow occlusion device 10 to be grasped by a delivery device as occlusion device 10 is guided through a catheter. However, the method of attachment to a delivery device is not so limited. Grasping knob 22 may be modified as needed to attach to any delivery device. For instance, grasping knob 22 may be fitted with threads so that it may be screwed onto a delivery device that is outfitted with threads.

Sheets 14, 16 are connected to wire frame 12 at arm pairs 24A-24F. Sheets 14, 16 may attach to arm pairs 24A-24F by folding each sheet 14, 16 over the perimeter of each arm pair 24A-24F and securing sheets 14, 16 in place. A variety of securing methods may be used such as suturing, heat treating, or laminating. Methods of attaching sheets 14, 16 to arm pairs 24A-24F are described more fully in FIGS. 6-9.

Sheets 14, 16 are preferably formed of a medical grade polymer, such as a high density polyvinyl alcohol (PVA) foam, offered under the trademark IVALON®. Other suitable materials, such as DACRON® may also be used. To minimize the chance of the occlusion device 10 causing a blood clot, sheets 14, 16 may be treated with a thrombosis-inhibiting material, such as heparin.

The size of sheets 14, 16 may vary to accommodate various sizes of defects. In some instances, it may be desirable to form sheets 14, 16 so that they are not both the same size. For instance, one sheet and its associated set of arms can be made smaller than the corresponding sheet and its associated set of arms. This is particularly useful in situations where occlusion device 10 is to be placed at a location in the heart which is close to other nearby cardiac structures. Making sheets 14, 16 different sizes may assist in providing optimal occlusion of a defect, without affecting other structures of the heart which may be nearby.

Occlusion device 10 is configured to be deployed through a catheter. More specifically, occlusion device 10 is constructed so that arm pairs 24A-24F are easily collapsible about proximal center post 18 and distal center post 20 to allow occlusion device 10 to be inserted through a catheter. Due to this construction, occlusion device 10 can be folded such that the arms attached to sheet 14 are folded in the axial direction A and the arms attached to sheet 16 are folded in an opposite axial direction B. Sheets 14, 16 are flexible and collapse as arm pairs 24A-24F are folded.

The shape of wire frame 12 results in occlusion device 10 having relatively little bulk. This makes it possible for arm pairs 24A-24F to collapse down to a very small diameter and therefore allows occlusion device 10 to be passed through a small guide catheter. This feature is essential for the treatment of children because they have smaller vessels than adults, and a very narrow catheter is need to deploy occlusion device 10 to the site of the defect.

Once occlusion device 10 is deployed across a defect in the heart, arm pairs 24A-24F and sheets 14, 16 unfold to form a seal around each side of the defect. To ensure occlusion device 10 returns to a shape capable of exerting enough pressure to seal the defect, arm pairs 24A-24F are made of a suitable material capable of shape memory, such as nickel-titanium alloy, commonly called Nitinol. Nitinol is preferably used because it is commercially available, very elastic, non-corrosive and has a fatigue life greater than that of stainless steel. To further ensure that arm pairs 24A-24F do not suffer from fatigue failures, one embodiment of the present invention comprises making wire arm pairs 24A-24F of stranded wire or cables.

Figure 2:
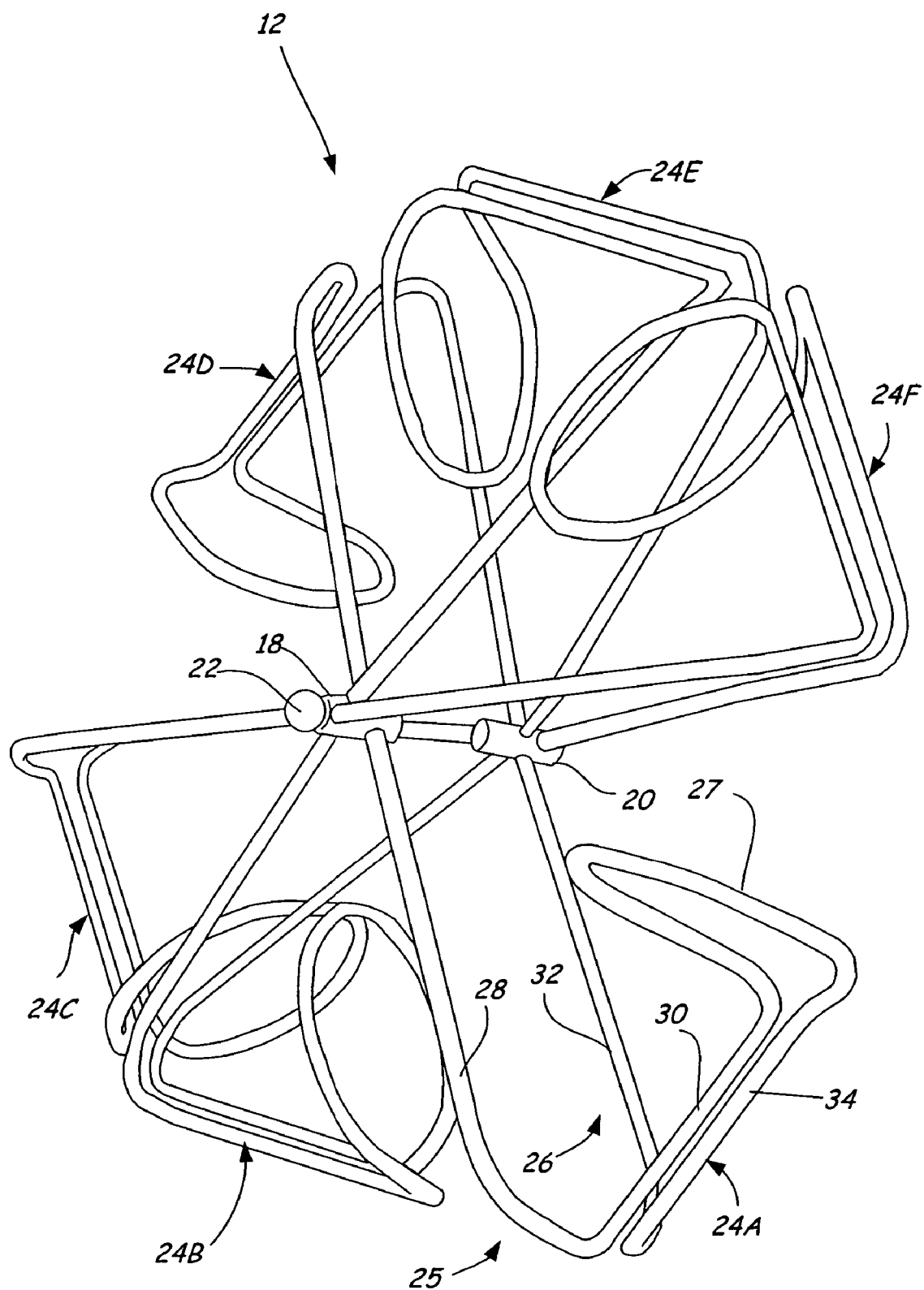
FIG. 2 is a perspective view of a wire frame of the occlusion device of FIG. 1.

FIG. 2 is a perspective view of wire frame 12. Shown in FIG. 2 is proximal center post 18, distal center post 20, grasping knob 22, and the six arm pairs 24A-24F. Each of the six arm pairs 24A-24F includes proximal arm 25, distal arm 26, and centering arc 27. Proximal arm 25 includes first radial portion 28 and first circumferential portion 30. Distal arm 26 includes second radial portion 32 and second circumferential portion. Proximal arm 25 and distal arm 26 are connected by centering arc 27.

First radial portion 28 extends radially outward from proximal center post 18. First circumferential portion 30 extends from the outer end of first radial portion 28 to the proximal end of centering arc 27. Second radial portion 32 extends radially outward from distal center post 20. Second circumferential portion 34 extends from the outer end of second radial portion 32 to the distal end of centering arc 27.

The six arm pairs 24A-24F are connected to proximal center post 18 and distal center post 20. Proximal center post 18 and distal center post 20 have holes drilled around their circumference. One method of connecting the six arm pairs 24A-24F to proximal center post 18 and distal center post 20 is to provide proximal center post 18 and distal center post 20 with drill holes through which the six arm pairs 24A-24F pass. For example with respect to arm pair 24A, proximal arm 25 is connected to proximal center post 18 by inserting first radial portion 28 into a hole drilled through proximal center post 18 and distal arm 26 is connected to distal center post 20 by inserting second radial portion 32 into a hole drilled through distal center post 20. Remaining arm pairs 24A-24F are then connected to proximal center post 18 and distal center post 20 in the same manner.

The six arm pairs 24A-24F may be formed of three wires. The three wires create the six arm pairs 24A-24F because proximal center post 18 and distal center post 20 divide each wire into two arm pairs 24A-24F when the wire passes through proximal center post 18 and distal center post 20. Alternatively, arm pairs 24A-24F may be formed of six wires or even one wire. Each arm pair 24A-24F is offset from adjacent arm pairs 24A-24F by 60°. This offsetting serves to more evenly space arm pairs 24A-24F, which helps to create a uniform seal around the defect.

Arm pairs 24A-24F are preferably subjected to precise pre-shaping to give them a "shape memory." The pre-shaping can be done either by machining, heat treating, or both. The shape memory helps to hold the strands together when arm pairs 24A-24F are formed of stranded wire or cable, and can be used to add pretension to arm pairs 24A-24F, so that they "remember" their shape even after undergoing a strong deformation when occlusion device 10 is passed through a catheter. The diameter of the wire that is used to form arm pairs 24A-24F must be small enough so that wire frame 12 flexible enough to collapse when occlusion device 10 is being loaded or retrieved. However, the wire must be stiff enough to allow arm pairs 24A-24F to lie as flat as possible against the patient's septum to create an effective seal.

The other parts of occlusion device 10 are likewise formed of suitable materials. More specifically, center posts 18,20 may be formed of platinum-iridium. However, the invention is not limited to these materials and any suitably biocompatible material will suffice.

Another feature of occlusion device 10 is that it is fully retrievable. In situations where occlusion device 10 is not properly deployed and must be retrieved into a catheter, it is possible to withdraw occlusion device 10 back into the catheter by grasping either grasping knob 22 on located on proximal center post 18 or by grasping any one of the proximal arms 25.

FIG. 3A is a perspective view of opposing arm pairs 24A and 24D of occlusion device 10 to better illustrate the shape of wire frame 12. Shown is proximal center post 18, distal center post 20, grasping knob 22, and opposing arm pairs 24A and 24D. Arm pair 24A is comprised of centering arc 27, first radial portion 28, first circumferential portion 30, second radial portion 32, and second circumferential portion 34. Likewise, arm pair 24D is also comprised of centering arc 27, first radial portion 28, first circumferential portion 30, second radial portion 32, and second circumferential portion 34.

Each arm pair 24A, 24D is connected to proximal center post 18 and distal center post 20. For example with respect to arm pair 24A, first radial portion 28 is connected to proximal center post 18 by inserting first radial portion 28 into a hole drilled through proximal center post 18 and second radial portion 32 is connected to distal center post 20 by inserting second radial portion 32 into a hole drilled through distal center post 20. Arm pair 24D is connected in the same manner on the opposite side of center posts 18, 20. While arm pairs 24A and 24D are depicted, opposing arm pairs 24B and 24D and opposing arm pairs 24C and 24F are positioned and connected identically. Once deployed, each proximal arm forms a mirror image of its opposing distal arm across a plane perpendicular to the center axis. The center axis extends from proximal center post 18 to distal center post 20.

FIG. 3B is a proximal end view of opposing arm pairs 24A, 24D of occlusion device 10 to better illustrate the shape of wire frame 12. Shown is grasping knob 22, proximate arm 25 of arm pair 24A, and proximate arm 25 of arm pair 24D (as shown in FIG. 1). From this perspective, all that is visible of arm pairs 24A, 24D is a portion of centering arc 27, first radial portion 28, first circumferential portion 30. As mentioned in FIG. 3A, while arm pairs 24A and 24D are depicted, opposing arm pairs 24B and 24D and opposing arm pairs 24C and 24F are positioned and connected identically.

FIG. 3C is a side view of opposing arm pairs 24A and 24D of occlusion device 10 to better illustrate the shape of wire frame 12. Shown is proximal center post 18, distal center post 20, grasping knob 22, and opposing arm pairs 24A, 24D. From this perspective, all that is visible of arm pairs 24A, 24D is centering arc 27, first radial portion 28, and second radial portion 30. As mentioned in FIGS. 3A and 3B, while arm pairs 24A and 24D are depicted, opposing arm pairs 24B and 24D and opposing arm pairs 24C and 24F are positioned and connected identically.

FIG. 4 is a proximal end view of wire frame 12 of occlusion device 10 illustrating occlusion device 10 (without sheets 14 and 16) deployed across defect 38. Shown is grasping knob 22, six arm pairs 24A-24F, atrial septal wall 36, and defect 38.

Arm pairs 24A-24F are shaped to form a self-centering portion of occlusion device 10. As previously explained in FIG. 2, each of the six arm pairs 24A-24F includes proximal arm 25, distal arm 26, and centering arc 27. Proximal arm 25 includes first radial portion 28 and first circumferential portion 30. Distal arm 26 includes second radial portion 32 and second circumferential portion 34. Proximal arm 25 and distal arm 26 are connected by centering arc 27.

First radial portion 28 extends radially outward from proximal center post 18. First circumferential portion 30 extends from the outer end of first radial portion 28 to the proximal end of centering arc 27. Second radial portion 32 extends radially outward from distal center post 20. Second circumferential portion 34 extends from the outer end of second radial portion 32 to the distal end of centering arc 27. First and second circumferential portions 30, 34 make direct contact with atrial septal wall 36.

The arm pairs 24A-24F allow occlusion device 10 to hug the tissue surrounding defect 38 to create a uniform seal around the opening of defect 38, which improves the sealing capabilities of occlusion device 10. This shape allows occlusion device 10 to maintain a low profile once occlusion device 10 is deployed, and also allows arm pairs 24A-24F to center occlusion device 10 within defect 38.

The size of occlusion device 10 is variable and should correspond to the rough size of defect 38 so that occlusion device 10 fits defect 38 properly. The ability of occlusion device 10 to self-center itself within defect 38 is improved when the size of occlusion device 10 is appropriate. If occlusion device 10 is properly sized and centered, the likelihood that defect 38 will be sealed is increased and the likelihood of blood shunting occurring is reduced.

FIG. 5 is a sectional view of wire frame 12 of occlusion device 10 along section 5-5 of FIG. 4 as it is deployed across defect 38 to better illustrate the position of wire frame 12 with respect to defect 38. Shown is proximal center post 18, distal center post 20, grasping knob 22, four of the six proximal arms 25, four of the six distal arms 26, centering arcs 27, atrial septal wall 36, defect 38, reinforced edge 39, a portion of right atrium, 40, and a portion of left atrium 42. The remaining proximal arms 25, the remaining distal arms 26, and the remaining centering arcs 27 cannot be seen from this perspective.

Upon deployment, the set of six proximal arms 25 contacts the proximal side of atrial septal wall 36 and the set of six distal arms contacts the distal side of the atrial septal wall 38. The set of six proximal arms 25 and the set of six distal arms 26 are connected by centering arcs 27, which extend through defect 38. Once occlusion device 10 is in place, the net forces existing between the set of six proximal arms 25 and the set of six distal arms 26 exert tension on centering arcs 27 spanning defect 38 and connecting the set of six proximal arms 25 and the set of six distal arms 26. Center posts 18,20 balance the opposing forces which culminate at centering arcs 27 which allows occlusion device 10 to self-center with respect to defect 38 being occluded. Due to the self-centering capabilities of occlusion device 10, defect 38 is more effectively sealed. In addition, the shape of wire frame 12 also allows occlusion device 10 to maintain a low profile against atrial septal wall 36, which minimizes the potential for blood clots.

FIG. 6 is a proximal end plan view of occlusion device 10, which demonstrates how occluding sheets 14, 16 may be attached to wire frame 12 as occlusion device 10 is deployed across defect 38. Shown is proximal occluding sheet 14, grasping knob 22, six proximal arms 25, atrial septal wall 36, defect 38, reinforced edge 43, and sutures 44.

In this embodiment, sheet 14 is attached to the outside of wire frame 12. Sheet 14 makes contact with three portions of each of proximal arm 25. On proximal arm 25, sheet 14 makes contact with first radial portion 28, first circumferential portion 30, and a portion of centering arc 27. The middle portion of centering arc 27 continues through the center of defect 38. A small hole is cut into sheet 14 to allow grasping knob 22 of proximal center post 18 to extend through. This helps to ensure sheet 14 is flat against arms 25 and also allows grasping knob 22 to be clasped in order to properly position occlusion device 10.

The diameter of proximal sheet 14 is slightly larger than that of wire frame 12. The larger diameter of sheet 14 extends beyond wire frame 12 and constitutes reinforcement edge material 43. Reinforcement edge material 43 allows this portion of sheet 14 to be folded over wire frame 12 to form a reinforced edge of double material around the perimeter of occlusion device 10. Once reinforcement edge material 43 has been folded over wire frame 12, it can be held in place though suturing, bonding, adhesives, heat treating, laminating, or any other suitable method. In FIG. 6, attachment of the sheets 14, 16 to proximal arms 25 and distal arms 26 is by sutures 44.

Alternatively, reinforced edge material 43 is created using a separate sheet of foam formed in a ring. The foam ring is sized to allow it to fold over the perimeter of occlusion device 10 and wire frame 12. The foam ring may be attached to the sheet 14 using any suitable method such as suturing, bonding, adhesive, heat treating, or laminating.

Once attached, reinforcement edge material 43 covers the exposed edges of occlusion device 10. Reinforcement edge material 43 acts as a cushion between the exposed metal edges of occlusion device 10 and the tissue surrounding defect 38, providing extra protection from pressure that occlusion device 10 exerts on the tissue.

Reinforced edge 43 also secures sheets 14, 16 to occlusion device 10. Often, in order to adequately seal defect 38, wire arm pairs 24A-24F must bend to accommodate the contours of the heart. Because sheets 14, 16 are sewn to wire arm pairs 24A-24F by sutures 44, sheets 14, 16 must accommodate the bending of wire arm pairs 24A-24F. In locations where some of wire arm pairs 24A-24F are bent by the contours of the heart, a portion of sheets 14, 16 may be stretched so that it experiences constant tension. This tension may cause sheets 14, 16 to tear, especially where the sutures are located. If sheets 14, 16 tear, the sealing ability of occlusion device 10 may be compromised. Reinforced edge 43 helps to prevent sheets 14, 16 from tearing at the areas where sheets 14, 16 are attached to wire frame 12 or are sutured. Because reinforcement edge 43 overlaps wire frame 12 and is then affixed to the rest of sheets 14, 16, it adds an additional 360° of continuous attachment of sheets 14, 16 to wire frame 12 of occlusion device 10, reducing the likelihood of tearing or detachment. The additional foam material along the perimeter of occlusion device 10 helps to distribute the tension on sheets 14, 16 along a continuum, instead of focusing tension at discrete attachment sites like the suture points.

FIG. 7 is a sectional view of occlusion device 10 along section 7-7 of FIG. 6, which demonstrates how sheets 14, 16 may be attached to wire frame 12 as occlusion device 10 is deployed across defect 38. Shown are proximal sheet 14, distal sheet 16, proximal center post 18, distal center post 20, grasping knob 22, four of the six proximal arms 25, four of the six distal arms 26, centering arcs 27, atrial septal wall 36, defect 38, a portion of right atrium 40, a portion of left atrium 42, and reinforced edge 43. The remaining proximal arms 25, the remaining distal arms 26, and the remaining centering arcs 27 cannot be seen from this perspective.

In this embodiment, sheets 14, 16 are attached to the outside of wire frame 12. Proximal sheet 14 lays flat against the outside portion of proximal arms 25 and distal sheet 16 lays flat against the outside portion of distal arms 26. A hole is cut in sheets 14, 16 to allow proximal center post 18, distal center post 20, and grasping knob 22 to extend through to the outside of sheets 14, 16. Reinforced edge 43 folds over proximal arms 25 and distal arms 26. Reinforcement edge 43 acts as a cushion between the exposed metal edges of wire frame 12 and the tissue surrounding defect 38, providing extra protection from pressure that occlusion device 10 exerts on the tissue.

Each centering arc 27 extends through defect 38 exerting tension on proximal arms 25 and the distal arms 26 and self-centering occlusion device 10. Proximal arms 25 and proximal sheet 14 make contact with atrial septal wall 36 of right atrium 40. Distal arms 26 and distal sheet 16 make contact with atrial septal wall 36 of left atrium 42. Since occlusion device 10 is able to effectively self-center and hug the tissue surrounding defect 38, it creates a uniform seal around the opening of defect 38, while maintaining a low profile against atrial septal wall 36.

FIG. 8 is a proximal end view of occlusion device 10, which demonstrates how occluding sheets 14,16 may be attached to wire frame 12 as occlusion device 10 is deployed across defect 38. Shown is proximal occluding sheet 14, grasping knob 22, six proximal arms 25, atrial septal wall 36, defect 38, reinforced edge 43, sutures 44, and slits 46.

In this embodiment, sheet 14 is attached to the inside of wire frame 12. Sheet 14 makes contact with one portion of each proximal arm 25. On each proximal arm 25, sheet 14 only makes contact with first circumferential portion 28 at a place where proximal arm 25 makes contact with atrial septal wall 36. Slits 46 are cut into the outer edge of sheet 14. This allows sheet 14 to be attached to wire frame 12 after wire frame 12 is shaped and assembled. Sheet 14 is attached to wire frame 12 by inserting each centering arc 27 into each slit 46. The middle portion of each centering arc 27 continues through the center of defect 38.

The diameter of proximal sheet 14 is slightly larger than that of wire frame 12. The larger diameter of sheet 14 extends beyond wire frame 12 and constitutes reinforcement edge 43. Reinforcement edge 43 allows this portion of sheet 14 to be folded over wire frame 12 to form a reinforced edge of double material around the perimeter of occlusion device 10. Once reinforcement edge 43 has been folded over wire frame 12, it can be held in place though suturing, bonding, adhesives, heat treating, laminating, or any other suitable method. In FIG. 8, attachment of the sheets 14, 16 to proximal arms 25 and distal arms 26 is by sutures 44.

Alternatively, reinforced edge 43 is created using a separate sheet of foam formed in a ring. The foam ring is sized to allow it to fold over the perimeter of occlusion device 10 and wire frame 12. The foam ring may be attached to the sheet 14 using any suitable method such as suturing, bonding, adhesive, heat treating, or laminating.

Once attached, reinforcement edge 43 covers the exposed edges of occlusion device 10. Reinforcement edge 43 acts as a cushion between the exposed metal edges of occlusion device 10 and the tissue surrounding defect 38, providing extra protection from pressure that occlusion device 10 exerts on the tissue.

FIG. 9 is a sectional view of occlusion device 10 along section 9-9 of FIG. 8, which demonstrates how occluding sheets 14,16 may be attached to wire frame 12 as occlusion device 10 is deployed across defect 38. Shown is proximal sheet 14, distal sheet 16, proximal center post 18, distal center post 20, grasping knob 22, four of the six proximal arms 25, four of the six distal arms 26, centering arcs 27, atrial septal wall 36, defect 38, a portion of right atrium 40, and a portion of left atrium 42, and reinforced edge 43. Remaining proximal arms 25, remaining distal arms 26, and remaining centering arcs 27 cannot be seen from this perspective.

In this embodiment, sheets 14,16 are attached to the inside of wire frame 12. Proximal sheet 14 lays flat against the defect 38 inside the proximal arms 25 and the distal sheet lays flat against the defect 38 inside the distal arms 25A, 25B, 25C, 25D, 25E, 25F. Slits 46 are cut in sheets 14,16 to allow sheets 14,16 to be attached to wire frame 12 after wire frame 12 is shaped and assembled. Sheet 14 is attached to each proximal arm 25 and each distal arm 26 by inserting each centering arc into slits 46. The middle portion of each centering arc, continues through the center of defect 38. Reinforced edge 43 folds over first circumferential portion 30 of each proximal arm 25 and each distal arm. Reinforcement edge 43 acts as a cushion between the exposed metal edges of wire frame 12 and the tissue surrounding defect 38, providing extra protection from pressure that occlusion device 10 exerts on the tissue.

Each centering arc 27 extends through defect 38 exerting tension on proximal arms 25 and distal arms 26 to self-center occlusion device 10. Proximal arms 25 and proximal sheet 14 make contact with atrial septal wall 36 of right atrium 40. Distal arms 27 and distal sheet 16 make contact with atrial septal wall 36 of left atrium 42. Since occlusion device 10 is able to effectively self-center and hug the tissue surrounding defect 38, it creates a uniform seal around the opening of defect 38, while maintaining a low profile against atrial septal wall 36.

As already explained, FIG. 7 shows occlusion device 10 with both sheets 14, 16 attached to the outside of wire frame 12, and FIG. 9 shows occlusion device 10 with both sheets 14, 16 attached to the inside of frame 12. However, any combination of these embodiments could be used. For example, two proximal sheets 14 and two distal sheets 16 could be attached to wire frame 12, with two sheets 14, 16 attached as described in FIG. 7 and two described in FIG. 9. Likewise, two sheets 14, 16 could be attached on one side of wire frame 12 and only one sheet 14, 16 could be attached on the other side of wire frame 12.

Although the present invention has been described with reference to preferred embodiments, workers skilled in the art will recognize that changes may be made in form and detail without departing from the spirit and scope of the invention.

The invention claimed is:

1. A self-centering occlusion device for occluding an aperture, the self-centering occlusion device comprising:
   a wire frame comprising first and second central supports defining a central axis, the central axis extending from the first central support to the second central support, and a plurality of opposing wire arm pairs emanating from the first and second central supports, wherein each opposing arm pair comprises two arm pairs, wherein each arm pair comprises:
      a first radially extending strut attached to the first central support;
      a first contact strut for contacting tissue on a first side of the aperture attached to and extending circumferentially from the first radially extending strut;
      a second radially extending strut attached to the second central support such that in a deployed state the second radially extending strut is configured as a generally mirror image of the first radially extending strut across a plane perpendicular to the central axis;
      a second contact strut for contacting tissue on a second side of the aperture attached to and extending circumferentially from the second radially extending strut such that in a deployed state the second contact strut is configured as a mirror image of the first contact strut across the plane perpendicular to the central axis; and
      a curvilinear centering arc extending between the first contact strut and the second contact strut, the centering arc being flexible and radially movable with respect to the central axis, wherein the centering arc comprises a flexible wire configured to loop around and hug an edge of the aperture and position the central axis of the device in an approximate center of the aperture; and
   sheets affixed to the wire frame.

2. The self-centering occlusion device of claim 1 wherein the wire frame further comprises an outer diameter, wherein the outer diameter is defined by each contact strut of each arm pair, and an inner diameter, wherein the inner diameter is defined by each centering arc of each arm pair.

3. The self-centering occlusion device of claim 1 and further comprising a grasping post located on the wire frame.

4. The self-centering occlusion device of claim 1 wherein the wire frame is formed of stranded wire.

5. The self-centering occlusion device of claim 1 wherein the wire frame is formed of a single wire.

6. The self-centering occlusion device of claim 1 wherein the sheets comprise polyvinyl alcohol foam.

7. The self-centering occlusion device of claim 1, wherein each opposing arm pair is integrally formed.

8. An occlusion device for occluding an aperture in the body, the occlusion device comprising:
   a first post;
   a second post aligned with the first post along a central axis, the central axis extending through and including the first and second posts;
   a plurality of opposing arm pairs connected to the first and second posts and having first and second portions configured to be generally in mirror-image alignment with one another across a plane perpendicular to the central axis when in a deployed state, wherein each opposing arm pair comprises two arm pairs, each arm pair comprises:
      a first contact strut extending in a circumferential direction for contacting tissue on a first side of the aperture;
      a first radial strut extending between the first post and the first contact strut;
      a second contact strut for contacting tissue on a second side of the aperture generally aligned with the first contact strut;
      a second radial strut extending between the second post and the second contact strut and generally aligned with the first radial strut; and
      a curvilinear arc extending between the first contact strut and the second contact strut and crossing the plane when in a deployed state, the arc being flexible and radially movable with respect to the central axis, wherein the arc comprises a flexible wire loop configured to extend through and hug an edge of the defect thereby applying self-centering forces through the opposing arm pairs to the first and second posts for positioning the central axis of the device centrally within the defect.

9. The occlusion device of claim 8 wherein the first contact strut and the second contact strut each extend in a generally circumferential direction from an outer end of the first radial strut and the second radial strut, respectively.

10. The occlusion device of claim 8 wherein the centering arc is configured to extend from a first side of the aperture through the aperture to a second side of the aperture.

11. The occlusion device of claim 8 wherein the plurality of opposing arm pairs comprises six arm pairs.

12. The occlusion device of claim 11 wherein the six arm pairs are formed of three wires.

13. The occlusion device of claim 11 wherein the six arm pairs are formed of a single wire.

14. The occlusion device of claim 8 wherein the first radial strut and the second radial strut are shaped to urge the first and second contact struts toward each other.

15. The occlusion device of claim 8 and further comprising a first sheet affixed to the first contact strut of each arm pair.

16. The occlusion device of claim 15 and further comprising a second sheet affixed to the second contact strut of each arm pair.

17. The occlusion device of claim 8, wherein each opposing arm pair, including the arcs, is integrally formed.

18. A frame for an occlusion device, the frame comprising:
first and second central supports;
a plurality of L-shaped proximal support arms for placement on a proximal side of a defect wherein each proximal support arm comprises a first radial strut extending radially outward from the first central support and a first circumferential strut extending circumferentially from a first bend located at an outer end of the first radial strut;
a plurality of L-shaped distal support arms for placement on a distal side of a defect wherein each distal support arm comprises a second radial strut extending radially outward from the second central support and a second circumferential strut extending circumferentially from a second bend located at an outer end of the second radial strut; wherein the plurality of L-shaped proximal support arms oppose the plurality of L-shaped distal support arms in a mirror-image relationship across the plane defined between the first and second central supports and substantially perpendicular to an axis extending between and including the first and second central supports; and
a plurality of curvilinear centering arcs connecting the plurality of L-shaped proximal support arms to the plurality of L-shaped distal support arms, each centering arc extending radially inward from each first circumferential strut and each second circumferential strut, the centering arcs being located outward from both the first and the second central supports, the centering arcs being flexible and radially movable with respect to the central axis, wherein an innermost portion of the centering arcs are configured to flex to self-center the occlusion device with respect to the defect.

19. The frame of claim 18 wherein the centering arcs are shaped to span across the defect to be occluded.

20. The frame of claim 18, wherein one of the plurality of L-shaped proximal support arms and one of the plurality of L-shaped distal support arms and one of the plurality of centering arcs are integrally formed.

* * * * *